United States Patent [19]

Daum et al.

[11] 4,053,598

[45] Oct. 11, 1977

[54] PREPARATION OF 2,4-DIOXO-1,2,3,4-TETRAHYDRO-s-TRIAZINO-[1,2-a]-BENZIMIDAZOLES

[75] Inventors: Werner Daum, Krefeld; Paul-Ernst Frohberger, Leverkusen, both of Germany

[73] Assignee: Bayer Aktiengesellschaft, Leverkusen, Germany

[21] Appl. No.: 694,418

[22] Filed: June 9, 1976

[30] Foreign Application Priority Data

June 21, 1975  Germany ............................ 2527677

[51] Int. Cl.$^2$ .................. C07D 413/14; A61K 31/53; A61K 31/535; C07D 487/04
[52] U.S. Cl. ............................. 424/248.56; 424/249; 544/113; 544/212
[58] Field of Search ...................... 260/249.5, 247.5 C; 424/249, 248.56

[56]  References Cited
U.S. PATENT DOCUMENTS 3,725,406   4/1973   Bose et al. .......................... 260/249.5
3,928,345  12/1975   Rochling et al. .................. 260/249.5

OTHER PUBLICATIONS

Schroeder et al., Chemical Abstracts, vol. 78, entry 159686K, 1973.
White et al., Chem. Abstracts, vol. 79, entry 101526n (1973).
Capuano et al., Chem. Ber., vol. 107, pp. 62–67 (1974).

Primary Examiner—John M. Ford
Attorney, Agent, or Firm—Burgess, Dinklage & Sprung

[57] ABSTRACT 2,4-Dioxo-1,2,3,4-tetrahydro-s-triazino-[1,2-a]-benzimidazoles of the formula

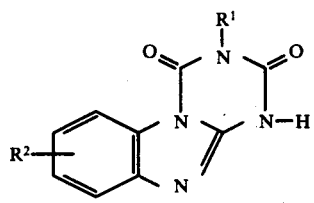

are produced by reacting a benzimidazole compound of the formula

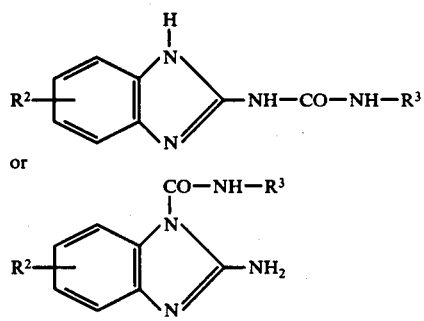

with a diphenyl carbonate of the formula

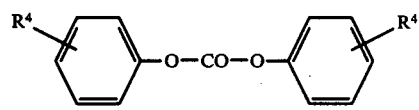

wherein
R$^1$ is optionally substituted alkyl or aryl, alkenyl or dialkylamino,
R$^2$ is hydrogen, alkyl or trifluoromethyl,
R$^3$ is any of the R$^1$ radicals or hydroxycarbonylalkyl, and
R$^4$ is hydrogen, alkyl or halogen.

The reaction can be effected employing the benzimidazole in impure form, without isolation, in the vessel in which it is formed. Those compounds wherein R$^1$ is a variously ω-substituted alkyl radical and R$^2$ is hydrogen or methyl are new and all the compounds exhibit fungicidal activity.

23 Claims, No Drawings

PREPARATION OF 2,4-DIOXO-1,2,3,4-TETRAHYDRO-s-TRIAZINO-[1,2-a]-BENZIMIDAZOLES

The present invention relates to a new process for the preparation of certain 2,4-dioxo-1,2,3,4-tetrahydro-s-triazino-[1,2-a]-benzimidazoles, some of which are known.

Some of the said benzimidazoles are disclosed in German Offenlegungsschrift (German Published Specification) No. 2,144,505, from which it is also known that they can be used as active compounds in biocidal agents for combating parasites and phytophathogenic fungi.

They are prepared by reacting o-phenylenediamine with cyanogen bromide in the presence of alkali metal bicarbonates, in accordance with the process known from U.S. Pat. No. 2,444,609 or from Beilsteins Handbuch der organischen Chemie (Beilstein's Handbook of Organic Chemistry), 4th edition, volume 26, page 497, and converting the resulting dioxotriazinobenzimidazoles, which are unsubstituted in the triazine ring, to the desired compounds in a second stage with the aid of alkylating agents. This process has the disadvantage that the reaction must be carried out in two stages. Furthermore, the first stage, that is the reaction of o-phenylenediamines with cyanogen bromide, is technically complicated, since working with cyanogen bromide demands increased safety precautions and, moreover, damage due to corrosion of the reaction vessels can occur. This damage can only be prevented by considerable technical effort.

The triazino-benzimidazoles can further be obtained in accordance with German Offenlegungsschrift (German Published Specification) No. 2,144,505 by reaction of amine-substituted benzimidazoles with isocyanates. However, the disadvantage of this process is that the isocyanates used are employed in excess in this reaction. This makes the process uneconomical, especially when isocyanates of complicated structure are used. Furthermore, the isocyanates of many amines are unknown or cannot be prepared in accordance with known methods of producing isocyanates. Furthermore, the excess of isocyanates present in the reaction results in substituted 1-aminocarbonyl-2,4-dioxo-1,2,3,4-tetrahydro-s-triazino-[1,2-a]-benzimidazoles also being formed, as by-products.

The triazino-benzimidazoles can also be obtained by reaction of carboxamide-substituted N-(benzimidazoly)-carbamic acid esters of the formula

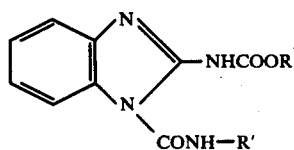

(I)

with at least an equimolar amount of an isocyanate. The disadvantages mentioned above apply to this process, since compounds of this type arise as intermediates in the reaction of N-benzimidazol-2-yl-carbamic acid esters with isocyanates.

The triazino-benzimidazoles can be obtained by reaction of benzimidazolylureas with phosgene in the presence of acid acceptors. However, the disadvantage of this process is that it must be carried out in the presence of tertiary amines. The amine hydrochlorides hereby produced are extremely corrosive, particularly as it is necessary to work at temperatures of up to 150° C.

The present invention now provides a process for the preparation of a 2,4-dioxo-1,2,3,4-tetrahydro-s-triazino-[1,2-a]-benzimidazole of the general formula

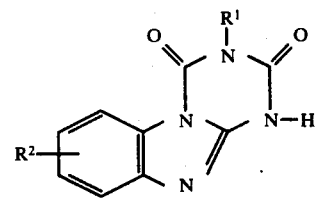

(II), in which
R$^1$ represents alkyl with 1-18 carbon atoms, which can optionally be substituted in the ω-position by chlorine, CN, aryl, alkoxycarbonyl, alkenoxycarbonyl, ω-alkylaminocarbony, ω-dialkylaminocarbonyl, phenoxycarbonyl, morpholino, piperidino, pyrrolidino or dialkylamino, or represents aryl which can optionally be substituted by chlorine, methyl or trifluoromethyl, or represents alkenyl with up to 18 carbon atoms, or represents dialkylamino, and
R$^2$ represents hydrogen, alkyl with 1-4 carbon atoms or trifluoromethyl, in which a benzimidazole compound of the general formula

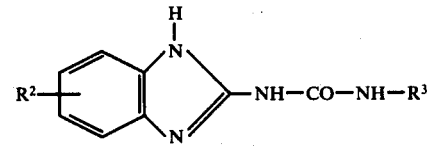

(III)

or of the general formula

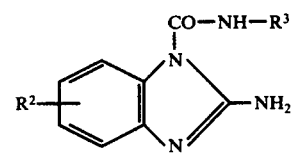

(IV), in which
R$^1$ and R$^2$ have the abovementioned meanings and
R$^3$ may have any of the meanings of R$^1$ or represent hydroxycarbonylalkyl with up to 18 methylene units, is reacted with a diphenyl carbonate of the general formula

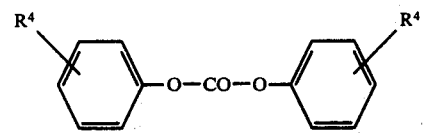

(V), in which
R$^4$ represents hydrogen, alkyl or halogen.

Advantageously the various aryl radicals of R$^1$ are phenyl and the alkoxy, alkenoxy and alkyl moieties of $R^1$ (apart from the alkyl of 1-18 carbon atoms), $R^3$ and $R^4$ have up to 4 carbon atoms.

Preferably, $R^1$ represents alkyl with 1-18 carbon atoms, or represents alkyl with 1-11 carbon atoms which is substituted in the ω-position by chlorine, CN, phenyl, alkoxycarbonyl with 1-4 carbon atoms in the alkoxy part, alkenoxycarbonyl with up to 3 carbon atoms in the alkenoxy part, phenoxycarbonyl, morpholino or dialkylamino with 1-4 carbon atoms per alkyl part, or represents propyl or ethyl substituted by pyrrolidine or piperidine, or represents dimethylamine; and $R^2$ represents hydrogen or methyl.

If compounds of the formula (IV) are employed, a conversion thereof into the compounds of the formula (III) occurs in the course of the reaction, prior to the cyclization.

If compounds of the formula (III) or (IV) in which $R^2$ is not hydrogen, are employed in the process according to the invention, the formation of two different dioxotetrahydro-s-triazino-benzimidazoles must be expected. If the starting materials contain a carboxyl group on the substituent $R^1$, the corresponding phenyl esters of the dioxotetrahydro-s-triazino-benzimidazoles are produced under the reaction conditions.

It is distinctly surprising that in the reaction of benzimidazoles of the formulae (III) and (IV) with a diphenyl carbonate of the formula (V) the 2,4-dioxo-1,2,3,4-tetrahydro-s-triazino-[1,2-a]-benzimidazoles, some of which are know, are produced. In view of the state of the art known from German Offenlegungsschrift (German Published Specification) No. 2,144,505 for the reaction of 1-(benzimidazol-2-yl)-ureas with phosgene (which is very reactive), which reaction requires temperatures of up to 150° C, the reaction with the comparatively unreactive diphenyl carbonate in a temperature range which is only slightly higher would not have been expected. On the other hand, the use of substantially higher reaction temperatures is inappropriate because of the decomposition of ureas which then occurs (see Methoden der Organischen Chemie (Methods of Organic Chemistry) [Houben-Weyl], volume 8, page 127, Stuttgart 1952, and French Patent Specification 1,387,756 according to Chemical Abstracts, 62, 14,900 b).

By following the process according to the present invention substituted products are preparable, whereas the process known from U.S. Pat. No. 2,444,609 only permits the preparation of unsubstituted compounds, which can only be converted in a further reaction step into the compounds preparable according to the invention.

Furthermore, the process according to the invention avoids working with cyanogen bromide and avoids the corrosion of the reaction apparatus which occurs when using that compound.

Compared to the process known from German Offenlegungsschrift (German Published Specification) No. 2,144,505, the process according to the present invention has the advantage that no isocyanates are used and instead the inexpensive industrial product diphenyl carbonate can be employed. As a result of this, the process according to the invention can be made economical especially when the isocyanates to be used in known processes can only be prepared with difficulty. Furthermore it is also possible to synthesize, by the process according to the invention, those dioxo-tetrahydrotriazino-benzimidazoles which are difficult or impossible to prepare by the other processes, because the isocyanates required for the process either have not been described in the literature or can only be prepared with difficulty.

Compared to the process for the reaction of benzimidazolyl-ureas with phosgene, also known from German Offenlegungsschrift (German Published Specification) No. 2,144,505, the process according to the invention has the advantages that the increased safety precautions for handling phosgene are unnecessary, corrosion of metal parts by amine hydrochlorides is avoided and dealkylation reactions do not occur.

A further advantage of the process according to the invention is that it is not essential to start from benzimidazole compounds of the formula (III) in the pure form. The reaction can be carried out in the form of a so-called one-pot reaction, by first reacting 2-aminobenzimidazole with diphenyl carbonate in phenol as the solvent to give the phenyl ester of ω-benzimidazol-2-yl-carbamic acid (see British patent specification No. 1,376,713), reacting this ester with an amine component to give the corresponding 1-(benzimidazol-2-yl)-urea of the formula (III), and then adding diphenyl carbonate to the entire reaction mixture, whereupon the reaction according to the invention takes place, with formation of the corresponsding 2,4-dioxo-1,2,3,4-tetrahydro-s-triazino-[1,2-a]-benzimidazoles.

Accordingly, the 2,4-dioxo-1,2,3,4-tetrahyro-s-triazino-[1,2-a]-benzimidazoles can, with the aid of the process according to the invention, be prepared more readily and more economically, and above all without great technical effort.

If 1-(benzimidazol-2-yl)-3-ω-butoxycarbonylmethylurea and diphenyl carbonate are used as starting materials, the course of the reaction can be represented by the following formula scheme:

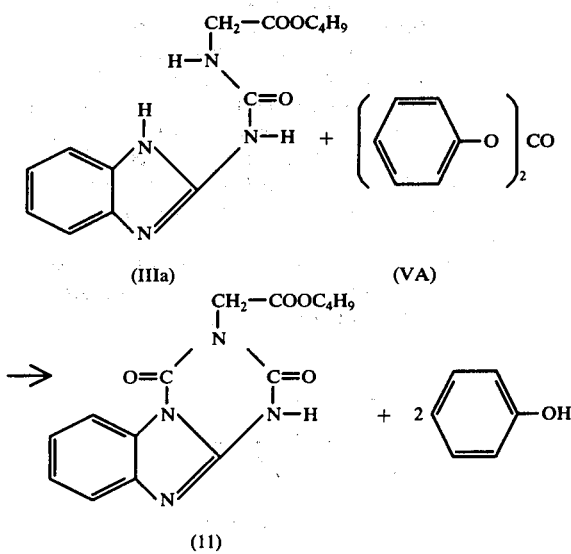

Particularly preferred starting compounds of the formula (III) and (IV) are those in which $R^1$ represents alkyl with 1-18 carbon atoms, or represents alkyl with 1-11 carbom atoms which is substituted in the ω-position by alkoxycarbonyl with 1-4 carbon atoms in the alkoxy part, by propenoxycarbonyl or by phenoxycarbonyl, by cyano, chlorine or N-morpholino, or represents dimethylamino. Preferably, $R^2$ represents hydrogen.

Particularly preferred starting compounds of the formula (V) are those in which $R^4$ represents hydrogen.

The following starting compounds of the general formulae (III) and (IV) are particularly suitable: 1,1-dimethyl- and 1,1-diethyl-4-(benzimidazol-2-yl)-semicarbazide; 1-(benzimidazol-2-yl)-3-(ω-morpholino-propyl)- , -3-(ω-morpholino-ethyl)-, -3-piperidino-propyl)-, -3-(pyrrolidino-propyl)-, -3-(ωdimethylamino-propyl)-urea; 1-ω-cyanoethylcarbamoyl-, 1-ω-cyanopentylcarbamoyl-, 1-ω-cyanoundecylcarbamoyl- and 1-butylcarbamoyl-2-amino-benzimidazole, and also 1-(benzimidazol-2-yl)-3-(ω-methyl-amino-carbonylme-thyl)-, -3-(ω-ethylaminocarbonylethyl)-, -3-(ω-propylaminocarbonylpropyl)-, -3-(ω-dimethylaminocarbonylpentyl)-, -3-(ω-butylaminocarbonylphenyl)-, 3-(ω-methylaminocarbonyldecyl)- and -3-(ω-dimethylaminocarbonylundecyl)-urea.

Examples of starting compounds of the general formula (V) are 2,2-dimethyl, 3,3-dimethyl-, 4,4-di-tert.-butyl, 2,2-dichloro-, 3,3-dichloro- and 4,4-dichloro-diphenyl carbonate, but, as implied above, diphenyl carbonate is particularly preferred.

Some of the compounds of the formula (III) used as starting materials are known. However, compounds of the formula (III) which have not yet been described in the literature can be prepared analogously to known processes. Such processes are known from U.S. Pat. No. 3,399,212. The compounds can also be prepared by reacting N-benzimidazol-2-yl-carbamic acid ketonoxide O-esters, which can be prepared in accordance with a process known from British patent specification No. 1,376,713, with an amine or an amine salt in the presence of a tertiary amine, such as triethylamine, or in the presence of an inorganic base, such as calcium carbonate.

Some of the compounds of the formula (IV) used as starting materials are known. Compounds of the formula (IV) which have not yet been described in the literature can however be prepared analogously to known processes. Such processes are known from U.S. Pat. Nos. 3,399,212, 3,673,210 and 3,794,728 and from Pellizari Gazzetta Chim. Ital. 49, pages 19–26. The compounds of the formula (IV) can be obtained by cautiously treating 2-aminobenzimidazoles with isocyanates.

In almost all cases, diphenyl carbonate can be employed as the starting material of the formula (V). If a phenol is used as the solvent during the reaction, the phenol liberated from the diphenyl carbonate during the cyclization reaction can be recovered in a simple manner, together with the solvent. Carbonates of the formula (V) which have not previously been described in the literature can be prepared, without difficulties, in accordance with known methods. Finally, it is also possible to use diphenyl carbonates prepared from various phenols. Processes for the preparation of carbonates of the formula (V) are known from Methoden der Organischen Chemie (Methods of Organic Chemistry) (Houben-Weyl), volume VIII, pages 106–107, Stuttgart 1952.

To carry out the process according to the invention, the (benzimidazol-2-yl)-urea derivative or the 1-aminocarbonyl-2-aminobenzimidazole derivative is heated to a temperature between about 140° and 220° C, preferably between about 160° and 190° C, with at least the equivalent amount, preferably about 1.1 to 1.4 times the equivalent amount, of the diphenyl carbonate in an inert higher-boiling solvent such as phenol, cresol, α-or β-naphthol, anisole, naphthalene, cumene or benzonitrile, advantageously in the presence of at least a catalytic amount, e.g. at least about 0.1g and preferably at least about 1 g mole per mole of benzimidazole compound, of an organic base, such as pyridine, dimethylbenzylamine or dimethylcyclohexylamine or of an inorganic base, such as potassium carbonate, calcium oxide or magnesium oxide, or of a catalytically active material, such as tin oxide. However, an organic base, such as N,N-dimethyldodecylamine, can also be used as the solvent.

Many 1-(benzimidazol-2-yl)-ureas are very sparingly soluble compounds; in most cases they are more sparingly soluble in the reaction medium than the corresponding dioxo-tetrahydro-triazino-benzimidazoles. In many cases, the starting products slowly dissolve during the reaction, and the resulting dioxotetrahydro-triazino-benzimidazoles may also precipitate. However, the behavior varies greatly because of the breadth of applicability of the reaction.

The course of the reaction can also be monitored by recording the IR spectra of KBr pressed tablets of samples of the reaction mixtures after removing the solvent from these, since dioxo-tetrahydro-triazino-benzimidazoles and 1-(benzimidazol-2-yl)-ureas differ considerably in the spectra of the KBr pressed tablets.

The 2,4-dioxo-1,2,3,4-tetrahydro-s-triazino-[1,2-a]-benzimidazoles are in most cases high-melting and sparingly soluble compounds which crystallize from the reaction mixtures at room temperature. If they do not, the reaction products must be concentrated by distilling off a part of the solvent.

The reaction produces are separated off and washed and triturated with a suitable solvent, such as acetonitrile, a lower alkanol or ketone. Because they are sparingly soluble, not all compounds can be purified by recrystallization.

2,4-Dioxo-1,2,3,4-tetrahydro-s-triazino-[1,2-a]-benzimidazoles form salts with alkali metal hydroxides or alkaline earth metal hydroxides or tertiary amines, such as trimethylamine, triethylamine and triethanolamine. Various compounds also form salts with acids, such as hydrogen halide acids, sulfuric acid, toluenesulfonic acid and the like. These salts are soluble in water, alcohols, acetonitrile or mixtures of these solvents. For purification, the crude product is dissolved under acid or alkaline conditions in the appropriate solvent and the resulting solution is filtered, if appropriate with addition of absorbents, such as active charcoals, silicas or fuller's earths. After adjusting the pH to a value which is generally between 6 and 4, the product is separated out. The dioxo-tetrahydro-triazino-benzimidazole derivative is washed until free from salt, and dried.

As already mentioned, some of the compounds obtainable by the process according to the invention are known. Compounds of the general formula (II) above, in which $R^1$ represents alkyl with up to 11 carbon atoms which is substituted in the ω-position by chlorine, cyano, alkoxycarbonyl with up to 4 carbon atoms in the alkoxy part, alkenoxycarbonyl with up to 3 carbon atoms in the alkenoxy part or N-morpholino, or represents dialkylamino with up to 4 carbon atoms in each alkyl group, and $R^2$ represents hydrogen or methyl, are new.

As is already known from German Offenlegungsschrift (German Published Specification) No. 2,144,505, the compounds which can be prepared by the process according to the invention have biocidal properties, such as, for example, a good fungitoxic activity. Because of their good toleration by plants, the compounds or their salts with bases or acids can be used for combating rust diseases, particularly the rust disease of cereals, which diseases are of practical importance. The rust diseases of cultivated plants which are of significance in agricultural practice include, for example, *Puccinia graminis, Puccinia recondita, Puccinia striiformis, Puccinia coronata, Uromyces fabae* and *Hemileia vastatrix.*

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides, or nematocides, insecticides, acaricides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1-95% by weight, and preferably 0.5-90% by weight, of the mixture, whereas carrier composition mixtures suitable for direct application or field application generally contemplate those in which the active compound is present in an amount substantially between about 0.0001-10%, preferably 0.01-1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001-95%, and preferably 0.01-95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. fungi, which comprises applying or controlling pests, e.g. fungi, which comprises applying to at least one of correspondingly (a) such fungi, and (b) the corresponding habitat thereof, i.e. the locus to be protected, e.g. to a growing crop, to an area where a crop is to be grown or to a domestic animal, a correspondingly combative or toxic amount, i.e. a fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course that the concentration of the particular active compound utilized in admixture with the carrier vehicle will depend upon the intended application. Therefore, in special cases it is possible to go above or below the aforementioned concentration ranges.

The process of the present invention and the activity of the compounds thereby produced are illustrated, without limitation, by the following examples:

EXAMPLE 1 a. Preparation of the intermediate

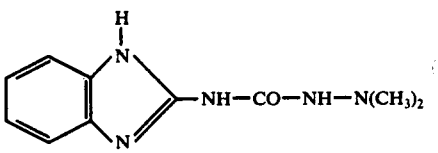

A mixture of 3 moles of benzimidazol-2-yl-carbamic acid phenyl ester and 2,100 g of phenol was stirred with 240 g of $N^1,N^1$-dimethylhydrazine for 7 hours at 70° C. After completion of the reaction, the reaction mixture was filtered and concentrated in vacuo. 1.6 liters of acetonitrile were added to the residue. The mixture was cooled to 0° C. The crystals were separated off and washed with acetonitrile and with water to which a small amount of a surfaceactive agent had been added. The crystals were dried at 100° C/3 mm Hg. Yield: 573 g of 1,1-dimethyl-4-(benzimidazol-2-yl)-semicarbazide, melting point > 330° C.

The IR spectrum of KBr pressed tablets showed, inter alia, strong bands at 1,512 and 1,575 cm$^{-1}$.

b.

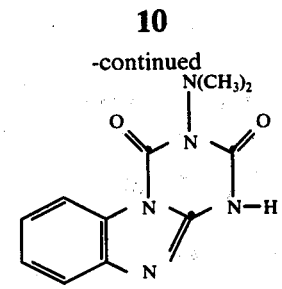

(1)

349 g of 1,1-dimethyl-4-(benzimidazol-2-yl)-semicarbazide, 428 g of diphenyl carbonate, 650 g of benzonitrile and 2,200 g of phenol were kept at 160° C for 24 hours. After completion of the reaction, the mixture of benzonitrile and phenol was very largely distilled off at 13 mm Hg. 900 ml of acetonitrile were added to the residue. The crystals were separated off, washed with acetonitrile and water and finally dried at 100° C/3 mm Hg. Yield: 360 g of crude 3-dimethylamino-2,4-dioxo-1,2,3,4-tetrahydro-s-triazino-[1,2-a]-benzimidazole.

For purification, the compound was dissolved in a boiling mixture of 5 liters of water, 3 liters of alcohol and 88 g of potassium hydroxide. The solution was filtered cold. The filtrate was adjusted to pH 4. The precipitate was filtered off and washed free from salt. Yield: 308 g of purified compound. Melting point > 330° C.

Calculated: N 28.56%.

Found: N 28.5%.

The IR spectrum in KBr showed strong carbonyl bands at 1,620 to 1,640 cm$^{-1}$, 1,695 to 1,705 cm$^{-1}$ and 1,745 cm$^{-1}$.

The following are obtained in an analogous manner:

Table 1

| Product according to the invention | Intermediate product |
|---|---|
| (2) 3-ω-Morpholinopropyl-2,4-dioxo-1,2,3,4-tetrahydro-s-triazino-[1,2-a]-benzimidazole<br>IR (KBr) 1,655, 1,705, 1,740 (s), 1,560 (m) cm$^{-1}$<br>Hydrochloride, melting point 269° C | 1-(Benzimidazol-2-yl)-3-(ω-morpholinopropyl)-urea<br>Melting point, about 319° C<br>IR (KBr) 1,535 – 1,600 cm$^{-1}$ (ss) |
| (3) Melting point 228° C, with decomposition | Melting point > 330° C<br>IR (KBr) 1,535 – 1,600, 1,635 sh<br>1,625, 1,700, 2,250 and<br>3,290 – 3,350 cm$^{-1}$ |
| (4) Melting point 258° C, with decomposition<br>IR (KBr) 1,610, 1,650 – 1,670,<br>1,710, 1,735 and 2,250 cm$^{-1}$ | Melting point > 330° C<br>IR (KBr) 1,535 – 1,600, 1,645 sh<br>1,630, 1,700, 2,250 and<br>3,300 – 3,350 cm$^{-1}$ |

Table 1-continued

| Product according to the invention | Intermediate product |
|---|---|
| (5) Compound with (CH$_2$)$_5$—CN substituent on triazine-dione fused to methylbenzene ring. Melting point 214° C, with decomposition, from ethylene glycol monoethyl ether. IR (KBr) 1,640 – 1,730 and 2,240 cm$^{-1}$ | Methylquinoxaline—NH—CO—NH—(CH$_2$)$_5$—CN. Melting point >330° C |
| (6) (CH$_2$)$_{11}$—CN substituent. Melting point 210° C, from toluene. IR(KBr) 1,655, 1,730 and 2,245 cm$^{-1}$ | Quinoxaline—NH—CO—NH—(CH$_2$)$_{11}$—CN. Melting point 202° C, with decomposition from ethylene glycol monomethyl ether |
| (7) (CH$_2$)$_6$—Cl substituent. Melting point 245° C, from butanol. IR (KBr) 1,660, 1,705 and 1,735 cm$^{-1}$ | Quinoxaline—NH—CO—NH—(CH$_2$)$_6$—Cl |
| (8) (CH$_2$)$_5$—CO—O—CH$_3$ substituent. Melting point 221° C, from acetonitrile. IR (KBr) 1,675, 1,705 and 1,740 cm$^{-1}$ | Quinoxaline—NH—CO—NH—(CH$_2$)$_5$—CO—O—CH$_3$. Melting point >330° C |
| (9) (CH$_2$)$_5$—CO—O—C$_2$H$_5$ substituent. Melting point 220° C, from alcohol. IR (KBr) 1,675, 1,705, and 1,735 sh 1,745 cm$^{-1}$ | Quinoxaline—NH—CO—NH—(CH$_2$)$_5$—CO—O—C$_2$H$_5$. Melting point >330° C, with decomposition |
| (10) (CH$_2$)$_{11}$—CO—O—CH$_3$ substituent. Melting point 167° C, from dibutyl ether. IR (KBr) 1,675, 1,710 and 1,745 cm$^{-1}$ | Quinoxaline—NH—CO—NH—(CH$_2$)$_{11}$—CO—O—CH$_3$. Melting point 184° C, with decomposition, from acetonitrile |
| (11) CH$_2$—CO—O—C$_4$H$_9$ substituent. Melting point 259° C, from butanol. IR (KBr) 1,660 sh 1,680, 1,715 and 1,740 cm$^{-1}$ | Quinoxaline—NH—CO—NH—CH$_2$—CO—O—C$_4$H$_9$. Melting point >330° C. IR (KBr) 1,582, 1,638, 1,700, 1,750 sh 1,745 and 3,310 cm$^{-1}$ |
| (12) CH$_2$—CO—O—CH$_3$ substituent. Melting point 252° C. IR (KBr) 1,695, 1,740 and 1,755 cm$^{-1}$ | Quinoxaline—NH—CO—NH—CH$_2$—CO—O—CH$_3$. Melting point 192 – 199° C, with decomposition. IR (KBr) 1,535 – 1,600, 1,642 sh 1,628, 1,700, 1,740 and 3,300 – 3,350 cm$^{-1}$ |

Table 1-continued

| Product according to the invention | Intermediate product |
|---|---|
| 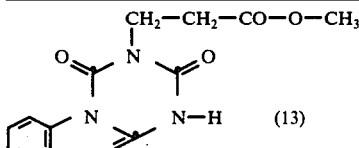 Melting point 251° C | 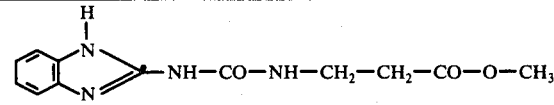 Melting point 212° C, with decomposition from acetonitrile, IR (KBr) 1,525 – 1,580, 1,640 sh 1,635, 1,715, 1,740 and 3,380 cm$^{-1}$ |
| 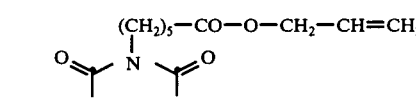 Melting point 136 – 139° C | 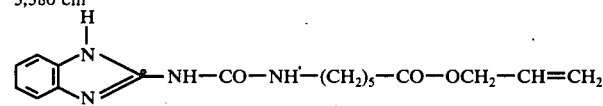 Melting point 187° C, with decomposition |
| 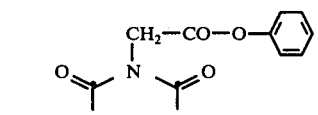 Melting point 280° C, with decomposition from dioxane IR (KBr) 1,690, 1,738 and 1,765 cm$^{-1}$ | 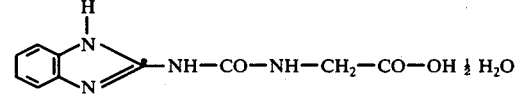 Melting point >320° C IR (KBr) 1,510 – 1,615, 1,650 – 1,660, 1,705 – 1,715 and 3,320 cm$^{-1}$ |

EXAMPLE 2

A mixture of 100 g of 2-aminobenzimidazole and 188 g of diphenyl carbonate, 390 g of phenol and 0.1 g of pyridine was kept for 1 hour at 60°–68° C and for 15 hours at 70° C. 63 g of dibutylamine was added and the reaction mixture was kept for 1 hour at 70° C and for 3 hours at 100° C. For the reaction, according to the invention, of the resulting 1-(benzimidazol-2-yl)-3-(butyl)-urea, 241 g of diphenyl carbonate, 200 g of benzonitrile and 0.2 g of potassium carbonate, were added and the mixture was heated to 160° C for 16 hours. The solvent was largely distilled off in vacuo and the residue was mixed with dibutyl ether. 3-Butyl-2,4-dioxo-1,2,3,4-tetrahydro-s-triazino-[1,2-a]-benzimidazole crystallized out as a crude product. This was separated off and washed with dibutyl ether. For purification, the crude product was boiled with 28 g of potassium hydroxide in 3 liters of water for 90 minutes. The hot solution was filtered. 3-Butyl-2,4-dioxo-1,2,3,4-tetrahydro-s-triazino-[1,2-a]-benzimidazole was isolated from the filtrate by acidification to a pH value of about 5. Melting point 275°–280° C.

EXAMPLE 3

Shoot treatment test/cereal rust/protective
(leaf-destructive mycosis)

To produce a suitable preparation of active compound, 0.25 part by weight of active compound was taken up in 25 parts by weight by dimethylformamide and 0.06 part by weight of emulsifier W and then 975 parts by weight of water were added. The concentrate was diluted with water to the desired final concentration of the spray liquor.

To test the protective activity, one-leaved young wheat plants of the Michigan Amber variety were inoculated with a uredospore suspensions of Puccinia recondita in 0.1% strength aqueous agar. After the spore suspension had dried on, the wheat plants were sprayed with the preparation of active compound until dew-moist and were placed, for incubation, in a greenhouse for 24 hours at about 20° C and 100% relative atmospheric humidity.

After 10 days' dwell time of the plants at a temperature of 20° C and 80–90% atmospheric humidity, the occurrence of rust pustules on the plant was evaluated. The degree of infection was expressed as a percentage of the infection of the untreated control plants. 0% denotes no infection and 100% denotes the same degree of infection as in the case of the untreated control. The active compound was more active, the lower was the degree of rust infection.

The active compounds, active compounds concentrations in the spray liquor and degrees of infection can be seen from the table which follows:

Table 2

| Shoot treatment test/cereal rust/protective | | |
|---|---|---|
| Active compound | Active compound concentration in the spray liquor in % by weight | Infection in % of the untreated control |
| untreated | — | 100 |
| 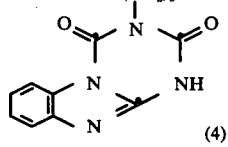 CH$_2$—NH—CS—S \ Zn / CH$_2$—NH—CS—s (known) | 0.025 0.01 | 93.8 100 |
| (4) | 0.025 0.01 | 25.0 25.0 |

Table 2-continued
Shoot treatment test/cereal rust/protective

| Active compound | Active compound concentration in the spray liquor in % by weight | Infection in % of the untreated control |
|---|---|---|
| 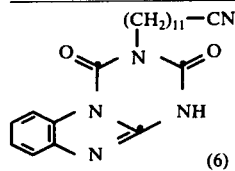 | 0.025<br>0.01 | 25.0<br>50.0 |

It will be appreciated that the instant specification and examples are set forth by way of illustration and not limitation, and that various modifications and changes may be made without departing from the spirit and scope of the present invention.

What we claim is:

1. A process for the preparation of a 2,4-dioxo-1,2,3,4-tetrahydro-s-triazino-[1,2-a]-benzimidazole of the formula

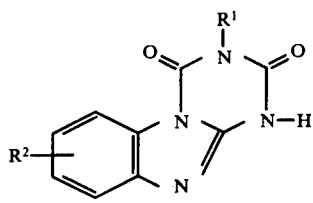

comprising reacting a benzimidazole compound of the formula

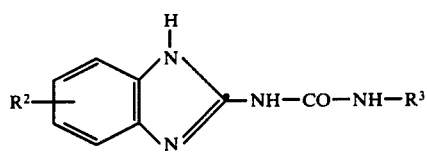

or of the formula

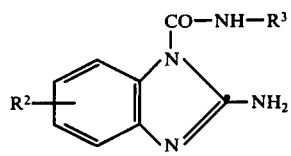

with a diphenyl carbonte of the formula

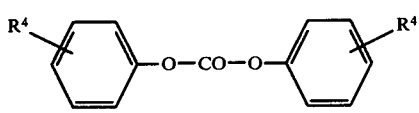

in which
$R^1$ represents alkyl with 1-18 carbon atoms which can optionally be substituted in the ω-position by chlorine, CN, phenyl, alkoxycarbonyl with 1 to 4 carbon atoms in the alkoxy part, alkenoxycarbonyl with 1 to 3 carbon atoms in the alkenoxy part, -alkylaminocarbonyl, phenoxycarbonyl, morpholino, piperidino, pyrrolidino or dialkylamino with 1 to 4 carbon atoms per alkyl part, or represents phenyl which can optionally be substituted by chlorine, methyl or trifluoromethyl, or represents alkenyl with up to 18 carbon atoms, or represents dialkylamino with 1 to 4 carbon atoms per alkyl part, and
$R^2$ represents hydrogen, alkyl with 1–4 carbon atoms or trifluoromethyl,
$R^3$ may have any of the meanings of $R^1$ or represents hydroxycarbonylalkyl with up to 18 methylene units, and
$R^4$ represents hydrogen, alkyl or halogen.

2. A process according to claim 1, in which the reaction is effected at a temperature of about 140° to 220° C.

3. A process according to claim 2, in which the reaction is effected at a temperature of about 160° to 190° C.

4. A process according to claim 1, in which the reaction is effected in the presence of an inert solvent.

5. A process according to claim 4 in which the solvent is phenol, cresol, α- or β-napthol, anisole, napthalene, cumene or benzonitrile.

6. A process according to claim 1, in which the reaction is effected in the presence of an organic or inorganic base.

7. A process according to claim 6, in which the base is pyridine, dimethylbenzylamine, dimethylcyclohexylamine, potassium carbonate, calcium oxide or magnesium oxide.

8. A process according to claim 1, in which the reaction is effected in a solvent which is an organic base.

9. A process according to claim 2, in which $R^3$ has any of the meanings of $R^1$ and is heated with about 1.1 to 1.4 times the equivalent amount of the diphenyl carbonate.

10. A process according to claim 1, in which $R^3$ is hydroxycarbonylalkyl and the benzimidazole compound is heated with about 2.1 to 2.4 times the equivalent amount of the diphenyl carbonate.

11. A process according to claim 1, in which the diphenyl carbonate is added to a solution in which the benzimidazole compound has been formed, the solution having been prepared by reacting a 2-aminobenzimidazole of the formula

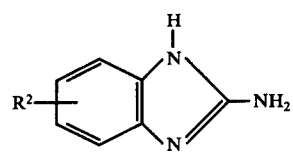

with a diphenylcarbonate of the formula

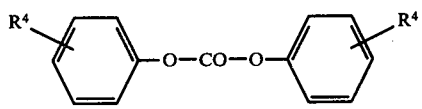

to form the corresponding phenyl ester of the corresponding ω-benzimidazol-2-yl-carbamic acid, and without isolation reacting this ester with an amine of the formula $NH_2—R^3$ to form the corresponding benzimidazole compound in solution.

12. A process according to claim 1, in which
$R^1$ represents alkyl with 1-18 carbon atoms, or represents alkyl with 1-11 carbon atoms which is substituted in the ω-position by chlorine, CN, phenyl, alkoxycarbonyl with 1-4 carbon atoms in the alkoxy part, alkenoxycarbonyl with up to 3 carbon atoms in the alkenoxy part, phenoxycarbonyl, morpholino or dialkylamino with 1-4 carbon atoms per alkyl part, or represents propyl or ethyl substituted by pyrrolidine or piperidine, or represents dimethylamine; and R² represents hydrogen or methyl.

13. A process according to claim 12, in which R² is hydrogen.

14. A process according to claim 12, in which R⁴ is hydrogen.

15. A process according to claim 12, in which
R⁴ is hydrogen,
R³ has any of the meanings of R¹, and
the benzimidazole compound is heated with about 1.1 to 1.4 times the equivalent amount of the diphenyl carbonate in the presence of an inert solvent and a base selected from the group consisting of pyridine, dimethylbenzylamine, dimethylcyclohexylamine, potassium carbonate, calcium oxide and magnesium oxide at a temperature of about 160° to 190° C.

16. A 2,4-dioxo-1,2,3,4-tetrahydro-s-triazino-[1,2-a]-benzimidazole of the formula

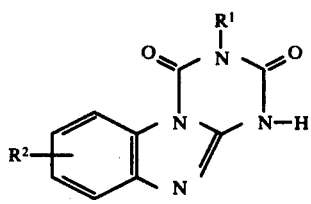

in which
R¹ represents alkyl with up to 11 carbon atoms which is substituted in the ω-position by chlorine, cyano, alkoxycarbonyl with up to 4 carbon atoms in the alkoxy part, alkenoxycarbonyl with up to 3 carbon atoms in the alkenoxy part or N-morpholino, or represents dialkylamino, with up to 4 carbon atoms in each alkyl group and
R² represents hydrogen or methyl.

17. A compound according to claim 16, wherein such compound is 3-ω-cyanopentyl-2,4-dioxo-1,2,3,4-tetrahydro-s-triazino-[1,2-a]-benzimidazole of the formula

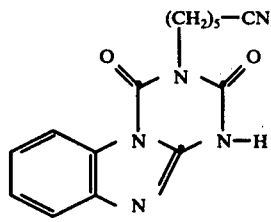

18. A compound according to claim 16, wherein such compound is 3-ω-cyanopentyl-2,4-dioxo-1,2,3,4-tetrahydro-s-triazino-]1,2-a]-6- or -7-methyl-benzimidazole of the formula

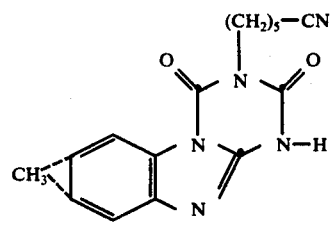

19. A compound according to claim 16, wherein such compound is 3-ω-chlorohexyl-2,4-dioxo-1,2,3,4-tetrahydro-s-triazino-[1,2-a]-benzimidazole of the formula

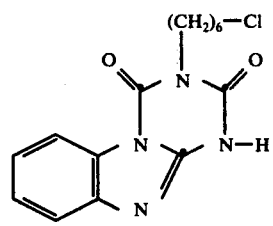

20. A compound according to claim 16, wherein such compound is 3-ω-methoxycarbonylpentyl-2,4-dioxo-1,2,3,4-tetrahydro-s-triazino-[1,2-a]-benzimidazole of the formula

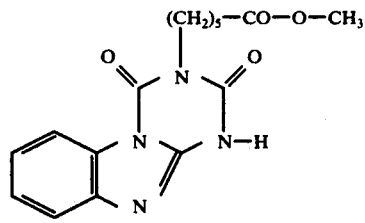

21. A compound according to claim 16, wherein such compound is 3-ω-ethoxycarbonylpentyl-2,4-dioxo-1,2,3,4-tetrahydro-s-triazino-[1,2-a]benzimidazole of the formula

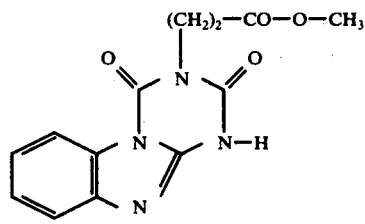

22. A fungicidal composition containing as active ingredient a fungicidally effective amount of a compound according to claim 16 in admixture with a diluent.

23. A method of combining fungi which comprises applying to the fungi or a fungus habitat a fungicially effective amount of a compound according to claim 16.

* * * * *